United States Patent
Rioux et al.

(10) Patent No.: US 8,540,666 B2
(45) Date of Patent: Sep. 24, 2013

(54) ECHOGENIC OCCLUSIVE BALLOON AND DELIVERY SYSTEM

(75) Inventors: Robert Rioux, Ashland, MA (US); David J. Sauvageau, Methuen, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1196 days.

(21) Appl. No.: 11/316,501

(22) Filed: Dec. 21, 2005

(65) Prior Publication Data
US 2007/0142770 A1   Jun. 21, 2007

(51) Int. Cl.
*A61M 29/00* (2006.01)

(52) U.S. Cl.
USPC ..................... 604/96.01; 604/93.01

(58) Field of Classification Search
USPC ............ 604/96.01, 97.01, 97.03, 103.01, 604/103.02, 103.06, 103.08, 103.1, 164.01, 604/164.03
See application file for complete search history.

(56) References Cited

U.S. PATENT DOCUMENTS

| | | | | |
|---|---|---|---|---|
| 4,531,937 A * | 7/1985 | Yates | ............................. | 604/539 |
| 5,102,402 A * | 4/1992 | Dror et al. | ....................... | 604/265 |
| 5,289,831 A | 3/1994 | Bosley | | |
| 5,327,891 A * | 7/1994 | Rammler | ....................... | 600/435 |
| 5,609,606 A * | 3/1997 | O'Boyle | ....................... | 606/194 |
| 5,807,327 A * | 9/1998 | Green et al. | ................. | 623/1.11 |
| 6,306,094 B1 * | 10/2001 | Joseph | ............................. | 600/458 |
| 6,364,855 B1 * | 4/2002 | Zappala | ....................... | 604/96.01 |
| 6,610,016 B1 * | 8/2003 | Violante et al. | ................ | 600/458 |
| 2002/0049465 A1 * | 4/2002 | Meyer et al. | ..................... | 606/195 |
| 2003/0180488 A1 * | 9/2003 | Lim et al. | ....................... | 428/35.2 |
| 2005/0075723 A1 * | 4/2005 | Schroeder et al. | ............. | 623/2.1 |
| 2005/0171525 A1 | 8/2005 | Rioux et al. | | |
| 2005/0209099 A1 * | 9/2005 | Chickering et al. | ........... | 502/314 |

FOREIGN PATENT DOCUMENTS

| | | |
|---|---|---|
| WO | WO 95/00198 A | 1/1995 |
| WO | WO 96/40347 A | 12/1996 |
| WO | WO 98/19713 A | 5/1998 |
| WO | WO 2006/094044 A | 9/2006 |

OTHER PUBLICATIONS

PCT International Search Report dated Nov. 22, 2007 for related International Application Serial No. PCT/US2006/061969 filed Dec. 13, 2006, Inventor Robert Rioux (5 pages).
PCT Written Opinion dated Nov. 22, 2007 for related International Application Serial No. PCT/US2006/061969 filed Dec. 13, 2006, Inventor Robert Rioux (7 pages).
International Preliminary Report on Patentability (Chapter I of the Patent Cooperation Treaty) from the International Bureau for the related International Application No. PCT/US2006/061969 dated Jul. 3, 2008 (7 pages).

* cited by examiner

*Primary Examiner* — Emily Schmidt
(74) *Attorney, Agent, or Firm* — Bingham McCutchen LLP

(57) ABSTRACT

A vessel occlusion apparatus includes an elongate shaft having a fluid delivery lumen; and an expandable member carried on a distal end portion of the shaft, the expandable member comprising a body defining an interior region, the interior region in communication with the fluid delivery lumen, the body comprising a wall having one or more embedded fluid pockets therein, each of the one or more pockets containing a fluid capable of being imaged, e.g., having echogenic qualities for detection using ultrasound imaging.

22 Claims, 3 Drawing Sheets

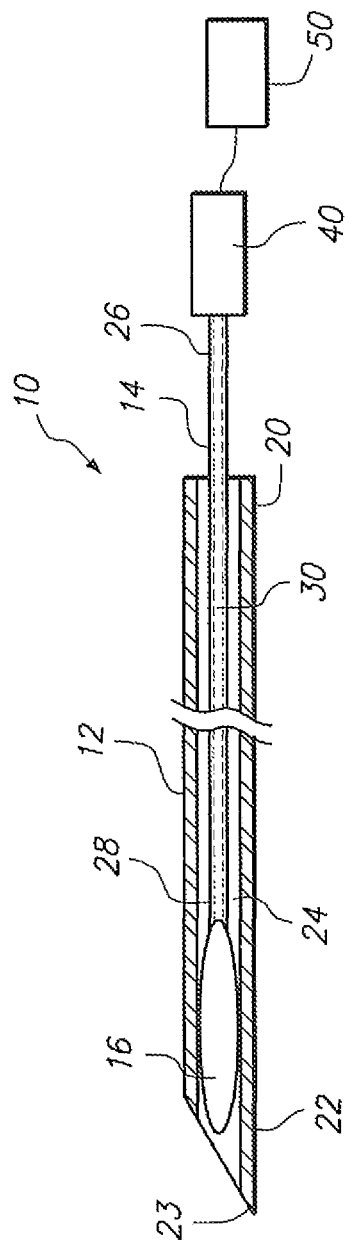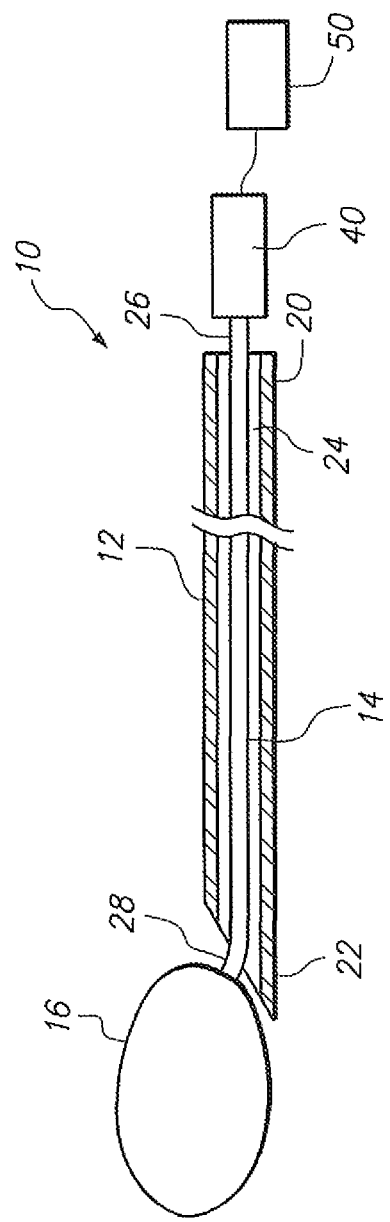

ECHOGENIC OCCLUSIVE BALLOON AND DELIVERY SYSTEM

FIELD OF INVENTION

The field of the application relates to medical devices, and more particularly, to an echogenic occlusive balloon and delivery system for use in performing medical procedures, such as liver resection.

BACKGROUND

Many liver resection procedures are performed every year. For example, a liver may need to be resected to remove a tumor, a cancerous cell, or a diseased part of a liver. Liver resection surgery is a risky procedure because after the liver is resected, the remaining liver may bleed significantly due to the vascularity nature of the liver. In some cases, a patient may even die from significant bleeding after a liver resection procedure.

In many medical procedures, balloons have been used to occlude blood vessels and aneurysms. However, balloons have not been used to occlude vessels within a liver during a liver resection procedure. This is because delivering a balloon within a target vessel inside an organ is difficult. In order to accurately position a balloon inside a patient, the balloon would need to be visualized using an imaging device such as an ultrasound imager. However, existing balloons are not made from a material that allows them to be clearly visualized using ultrasound. Sometimes, after the balloon is inflated with liquid, the balloon remains very difficult to be imaged with ultrasound. This is because liquid within the balloon is not echogenic, thereby preventing a clear ultrasound image of the balloon from being obtained.

Sometimes, in order to aid a physician to visualize the balloon after the balloon has been placed in a patient's body, the balloon can include a radio-opaque marker secured thereto. The radio-opaque marker is then imaged using an imaging device located outside the patient's body. However, adding the radio-opaque marker to the balloon increases a manufacturing cost of the balloon. In addition, there is a risk that the radio-opaque marker may become detached from the balloon while the balloon inside the patient's body.

Other medical devices also use radio-opaque markers to assist a physician in positioning and/or confirming a position of the devices. For example, the catheter used to deliver the balloon may also include a radio-opaque marker secured to a distal end of the catheter. During use, the radio-opaque marker at the catheter can be imaged using an imaging device, thereby allowing a physician to steer the catheter distal end to target area within a patient's body. However, the use of the radio-opaque markers in these device increases the manufacturing cost of these devices, and there is a risk that a marker may become detached from a device while the device is inside the patient's body.

SUMMARY

In accordance with one embodiment, a vessel occlusion apparatus includes an elongate shaft with an expandable member carried on a distal end portion of the shaft, the expandable member comprising a body defining an interior region, the interior region in communication with the fluid delivery lumen, the body comprising a wall having one or more embedded fluid pockets therein.

In accordance with another embodiment, an elongate tubular delivery member is provided, the tubular member having a proximal portion, a distal portion, a lumen extending between the proximal and distal portions, and a wall defining at least a portion of the distal portion of the tubular member, the wall having one or more embedded fluid pockets therein.

In accordance with yet another embodiment, a vessel occlusion system includes, in combination, an echogenic occlusive balloon apparatus and an echogenic delivery apparatus. The balloon apparatus comprises an elongate shaft having a fluid delivery lumen, and an expandable balloon carried on a distal end portion of the shaft, the balloon comprising a balloon body defining an interior region in communication with the fluid delivery lumen, the balloon body comprising a wall having one or more embedded fluid pockets therein. The delivery lumen comprises an elongate tubular delivery member having a proximal portion, a distal portion, a lumen extending between the proximal and distal portions and sized to accommodate insertion of the balloon apparatus there through, and a wall defining at least a portion of the distal portion of the tubular delivery member, the tubular member wall having one or more embedded fluid pockets.

Other and further aspects and features of the embodiments will be evident from reading the following description of the embodiments.

BRIEF DESCRIPTION OF THE DRAWINGS

The drawings illustrate the design and utility of embodiments of the application, in which similar elements are referred to by common reference numerals. In order to better appreciate how advantages and objects of various embodiments are obtained, a more particular description of the embodiments are illustrated in the accompanying drawings. Understanding that these drawings depict only typical embodiments of the application and are not therefore to be considered limiting its scope, the embodiments will be described and explained with additional specificity and detail through the use of the accompanying drawings.

FIG. 1 illustrates an vessel occlusion system in accordance with some embodiments, showing the vessel occlusion system having a balloon confined within a tubular member;

FIG. 2 illustrates the vessel occlusion system of FIG. 1, showing the balloon deployed out of a lumen of the tubular member;

DESCRIPTION OF THE EMBODIMENTS

Figure 4:
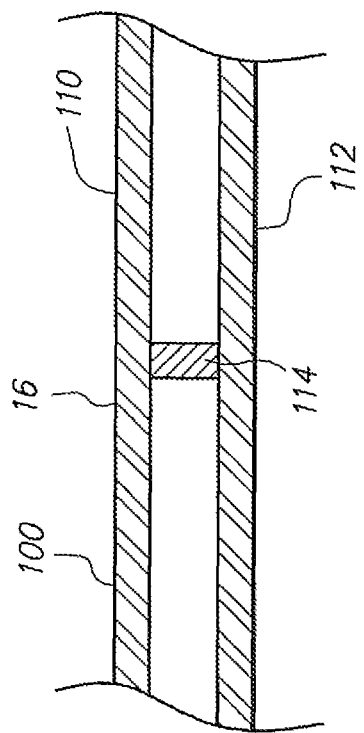
FIG. 4 is a sectional view of a wall of the balloon of FIG. 1 in accordance with other embodiments.

FIG. 1 illustrates a vessel occlusion system 10 in accordance with some embodiments. The vessel occlusion system 10 includes a tubular member 12, a shaft 14, and a balloon 16.

The tubular member 12 has a proximal end 20, a distal end, 22, and a lumen 24 extending between the proximal and distal ends 20, 22. In the illustrated embodiments, the distal end 22 has a sharp distal tip 23 for puncturing tissue. In other embodiments, the distal end 22 has a blunt tip. The tubular member 12 can be made from a variety of materials, such as a polymer, a metal, or an alloy. In the illustrated embodiments, the tubular member 12 has a rigid construction, which prevents the tubular member 12 from being bent. In other embodiments, the tubular member 12 has a flexible construction, which allows the tubular member 12 to be bent during use. For example, the tubular member 12 can be made from a malleable material that allows the tubular member to be bent to a desired shape by a physician. In another example, the tubular member 12 is in a form of a catheter body, which allows the tubular member to be steered through a vessel during use.

The shaft 14 is disposed at least partially within the tubular member lumen 24, and has a proximal end 26, a distal end 28, and a lumen 30 extending between the proximal and distal ends 26, 28. The shaft 14 can be made from a variety of materials, such as a polymer, a metal, or an alloy. In the illustrated embodiments, the shaft 14 has a flexible construction, which allows the shaft 14 to be bent during use. Alternatively, the shaft 14 can have a rigid construction. The system 10 further includes a handle 40 secured to the shaft proximal end 26, which allows a physician to manipulate the shaft 14. Alternatively, the handle 40 is optional, and the system 10 does not include the handle 40. In the illustrated embodiments, the system 10 also includes a fluid source 50, which is coupled to the proximal end 26, and is in fluid communication with the shaft lumen 30. During use, the fluid source 50 delivers fluid, such as saline, to the balloon 16 to thereby inflate the balloon 16.

The balloon 16 is secured to the distal end 28 of the shaft 14. When the balloon 16 is not inflated, it has a deflated configuration, which allows it to be housed within the tubular member lumen 24. The balloon 16 can be deployed from the distal end 22 by advancing the shaft 14 distally relative to the tubular member 12, and can be inflated to assume an expanded configuration (FIG. 2).

Figure 3:
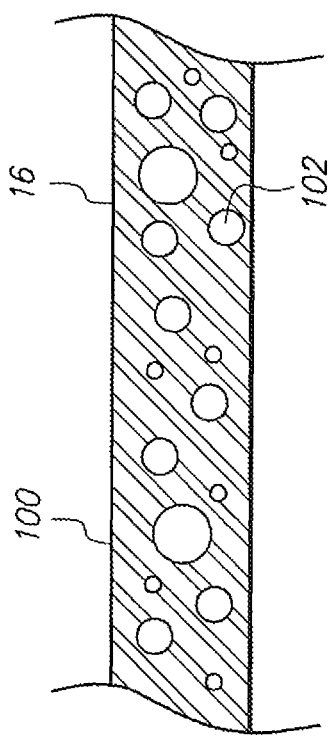
FIG. 3 is a sectional view of a wall of the balloon of FIG. 1 in accordance with some embodiments.

FIG. 3 illustrates a cross sectional view of a wall 100 of the balloon 16. The balloon wall 100 includes a plurality of fluid pockets 102, which allows the balloon wall 100 to be imaged by ultrasound during use. As used in this specification, the term "fluid pocket" refers to a pocket of gas, which may or may not be air, or a pocket of liquid. In the illustrated embodiments, the fluid pockets 102 are distributed around the entire wall 100 that forms the balloon 12. Alternatively, the fluid pockets 102 are only located within a part of the wall 100 that forms the distal portion of the balloon 12. Also, in the illustrated embodiments, the volume of the fluid pockets 102 within a unit length of the wall 100 is at least 10%, and more preferably, more than 50% of the volume of the wall in the unit length. Having such volume quantity of the fluid pockets allows a substantial cross section of the balloon wall 100 to be imaged using ultrasound. In other embodiments, the volume of the fluid pockets 102 within a unit length of the wall 100 can be other percentage values of the volume of the wall in the unit length.

It should be noted that the configuration of the fluid pockets 102 is not limited to the example shown in the figure, and that the fluid pockets 102 can have other configurations in other embodiments. For example, instead of having a circular shape, each of the fluid pockets 102 can have an elongated shape that extends a distance along a length of at least a portion of the balloon wall 100 (FIG. 4). Such configuration allows a continuous portion of the balloon wall 100 to be imaged using ultrasound energy. In some embodiments, the elongated fluid pockets 102 can be created by securing a first sheet 110 of material to a second sheet 112 of material using an adhesive 114 at selected locations. Other techniques known in the art of balloon making can also be used. In other embodiments, instead of elongated fluid pockets 102, the balloon 16 can have fluid pockets 102 having other shapes, such as an irregular shape.

The balloon 16 can be made using a variety of procedures. In some embodiments, the balloon 16 can be made using a mandrel molding technique. In such cases, a mandrel, the external shape and size of which mimics the desired shape and size, in its expanded mode, of the balloon to be created, is dipped one or more times into a solution of the substance from which the balloon body is to be formed until a desired wall thickness is achieved. The balloon body is allowed to dry on the mandrel and is then removed. The solution can be any material known in the art of balloon making. Before the mandrel is dipped into the solution, gas can be introduced into the solution. For example, the solution can be stirred or agitated to thereby introduce air into the solution. Alternatively, one or more tubes can be inserted into the solution to blow air into the solution. Because the solution has a plurality of fluid pockets, the formed balloon body will have a plurality of fluid pockets, as described in embodiments herein.

In other embodiments, the balloon 16 can be formed using expansion or blow molding. Here, a precursor body made of a desired substance, e.g., a piece of polyester tubing, is placed into a mold, the inner dimensions of which, like the external dimensions of the mandrel, are the desired size and shape of the expanded mode balloon body to be formed. The precursor body includes fluid pockets. One end of the tube is closed off and a fluid, such as a pressurized gas, is introduced through the open end of the tube, causing it to inflate. The mold is heated or, alternatively, it is ported to permit introduction of a heated fluid. In either case, when the tube comes in contact with the interior surface of the mold or when it contacts the heated fluid it, too, is heated and thereupon softened such that, when brought into contact with the inner surface of the mold, it conforms to its dimensions. The system is then cooled to permanently set the expanded size and shape of the balloon body to that of the mold. Because the precursor body has a plurality of fluid pockets, the formed balloon body will have a plurality of fluid pockets, as described in embodiments herein.

Figure 6:
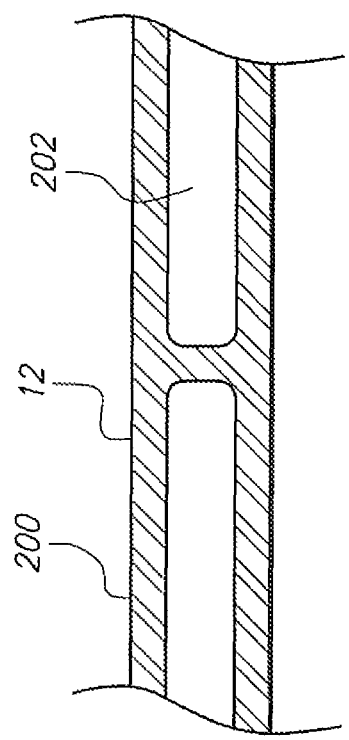
FIG. 6 is a sectional view of a wall of the tubular member of FIG. 1 in accordance with other embodiments.
Figure 5:
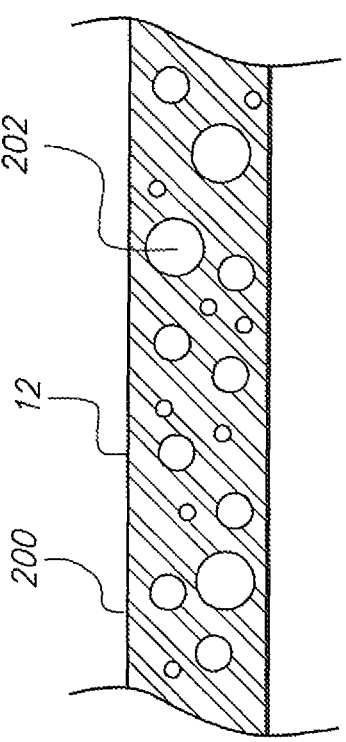
FIG. 5 is a sectional view of a wall of the tubular member of FIG. 1 in accordance with some embodiments.

In other embodiments, instead of, or in addition to, the balloon 12 having fluid pockets 102, one or both of the tubular member 12 and the shaft 14 can also include a plurality of fluid pockets, which allows the tubular member 12 and/or the shaft 14 to be imaged by acoustic energy during use. For example, in some embodiments, the wall 200 of the tubular member 12 can include a plurality of fluid pockets 202 (FIG. 5). In the illustrated embodiments, the fluid pockets 202 are located along a substantial portion (e.g., more than 50%) of a length of the tubular member 12, thereby allowing a substantial portion of the length of the tubular member 12 to be imaged by ultrasound energy. In other embodiments, the fluid pockets 202 are located at the distal end 22 of the tubular member 12, which allows the distal end 22 of the tubular member 12 to be imaged. If the distal end 22 has the sharp distal tip 23, the fluid pockets 202 allow the distal tip 23 to be imaged using ultrasound. It should be noted that the configuration of the fluid pockets 202 is not limited to the example shown in the figure, and that the fluid pockets 202 can have other configurations in other embodiments. For example, instead of having a circular shape, each of the fluid pockets 202 can have a rectangular shape (FIG. 6), or any of other shapes.

In the illustrated embodiments, the volume of the fluid pockets 202 within a unit length of the wall 200 is at least 10%, and more preferably, more than 50% of the volume of the wall in the unit length. Having such volume quantity of the fluid pockets allows a substantial cross section of the tubular member wall 200 to be imaged using ultrasound. In other embodiments, the volume of the fluid pockets 202 within a unit length of the wall 200 can be other percentage values of the volume of the wall in the unit length.

Various techniques can be used to form the tubular member 12 having a plurality of fluid pockets. In some embodiments, the tubular member 12 can be extruded from a material having a plurality of fluid pockets. In other embodiments, the tubular member 12 can be formed from a sheet of material having a plurality of fluid pockets. In such cases, the sheet can be rolled into a tubular shape to form the tubular member 12. In further embodiments, two tubular structures can be positioned coaxially relative to each other, and are secured to each other at certain locations. In such cases, the outer tubular structure forms the exterior surface of the tubular member 12, and the inner tubular structure forms the interior surface of the tubular member 12, with the spacing between the outer and inner tubular structures being the fluid pocket(s) 202.

In any of the embodiments of the system 10 described herein, the system 10 can further include a steering mechanism for steering the shaft distal end 28. For example, in some embodiments, the system 10 can further include one or more steering wires (not shown) secured to the distal end 28. The steering wire(s) can be housed within the shaft lumen 30, or within a wall of the shaft 14. During use, the steering wire can be pulled from a distal end (e.g., using a knob at the handle 40), to thereby steer the shaft distal end 28.

It should be noted that the system 10 is not necessarily limited to the configurations described previously, and that the system 10 can have other configurations in other embodiments. For example, in other embodiments, the balloon 16 can have different shapes and/or sizes. In further embodiments, instead of the balloon 16, the system 10 can include another expandable member. For example, the system 10 can include an expandable cage (not shown) secured to the distal end 28 of the shaft 14, and a sheet of material covering the cage. The sheet of material may include one or more fluid pockets, which allows the sheet to be imaged by ultrasound during use. The cage has a collapsed configuration when housed within the lumen 24 of the tubular member 12, and expands to form an expanded configuration when outside the lumen 24. In other embodiments, the system 10 does not include the tubular member 12. Instead, the balloon 16 and the shaft 14 can be used with other devices, such as an introducer sheath.

FIGS. 7A-7D illustrate a method of treating tissue using the treatment system 10 of FIG. 1 in accordance with some embodiments. The method will be described with reference to treating liver tissue. However, in other embodiments, the method can be similarly performed to treat tissue at other parts of a body.

Figure 7A:
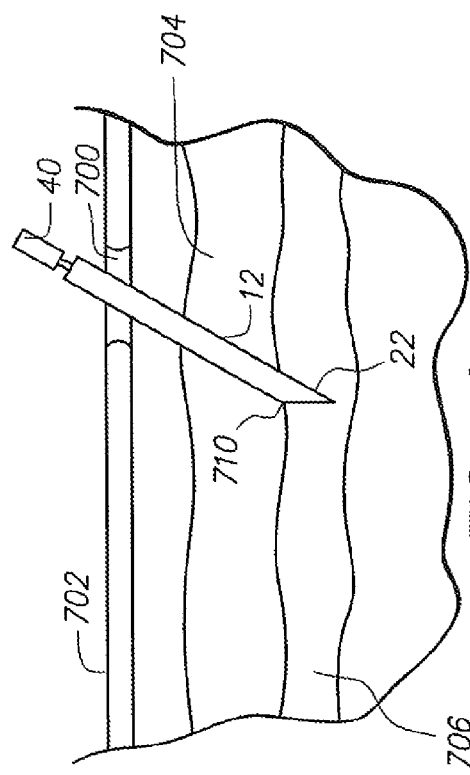
FIGS. 7A-7D illustrates a method of occluding a vessel using the vessel occlusion system of FIG. 1 in accordance with some embodiments.

First, an incision is made to create an opening 700 at a patient's skin 702, and the tubular member 12 is inserted through the opening 700 to reach a liver 704 (FIG. 7A). In the illustrated embodiments, the distal end 22 of the tubular member 12 has the sharp tip 23, and therefore, can be used to puncture the liver 704. The tubular member 12 is then advanced until the distal tip 23 puncture a target vessel 706 in the liver 704, thereby creating a punctured opening 710 at the vessel wall. As shown in FIG. 7A, only one side of the vessel 706 is punctured. In the illustrated embodiments, the tubular member 12 is rigid, which prevents the tubular member 12 from bending as the tubular member 12 is inserted at least partially through the liver 704. This in turn, allows the distal end 22 of the tubular member 12 to be positioned accurately within the liver 704. In other embodiments, if the tubular member 12 is flexible, it can be inserted into a vessel that leads to a target site, such as a heart.

In some embodiments, the distal end 22 of the wall of the tubular member 12 includes a plurality of fluid pockets 202, such as gas, which allows the distal end 22 to be imaged by an ultrasound imaging device while the distal end 22 is being positioned. In other embodiments, the fluid pockets 202 include a radio-opaque liquid (e.g., liquid having radio-opaque particles), which allows the distal end 22 to be imaged using other imaging technique. In further embodiments, the wall of the tubular member 12 does not include the plurality of fluid pockets 202. In such cases, the tubular member 12 can include a radio-opaque marker (e.g., in a form of a ring) that is secured to the distal end 22. The radio-opaque marker can be imaged by a fluoroscope or a x-ray device, which allows a physician to determine the position of the distal end 22 within the liver 704.

Figure 7B:
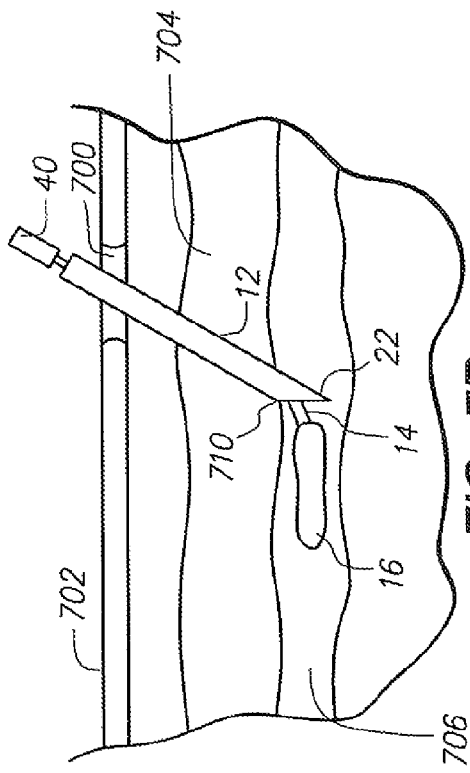

In the illustrated embodiments, before the balloon 16 is deployed at the target site, the balloon 16 is housed within the lumen 24 of the tubular member 12, and has a deflated configuration. After the distal end 22 is positioned at a desired position, the shaft 14 is advanced distally relative to the tubular member 12 to thereby push the balloon 16 out of the distal end 22 (FIG. 7B). As shown in the figure, the tapered configuration of the distal end 22 biases the balloon 16 to move towards one direction (e.g., upstream, which is the left side in the example) within the vessel 706, as the balloon 16 exits from the distal end 22. Alternatively, the tubular member 12 can be rotated such that the distal opening at the distal end 22 points towards another direction (e.g., a downstream direction). In some embodiments, the distal end 28 of the shaft 14 is steerable. In such cases, the distal end 28 of the shaft 14 can be steered to position the balloon 16 after the balloon 16 exits from the distal end 22. In other embodiments, the distal end 28 of the shaft 14 has a pre-bent configuration. In such cases, after the balloon 16 exits from the distal end 22 of the tubular member 12, the bent distal end 28 of the shaft 14 will automatically turn the balloon 16 towards the direction of the bent.

In other embodiments, the distal end 22 does not have the sharp tip 23. In such cases, a needle (not shown) can be inserted within the lumen 24 of the tubular member 12 and exits from the distal end 22. The needle is then used to pierce into the liver tissue. The needle and the tubular member 12 are advanced distally together until the needle punctures the vessel 706 to create the opening 710. The distal end 22 of the tubular member 12 is then further advanced into the opening 710 until the distal end 22 is located within the vessel 706. Next, the balloon 16 and the shaft 14 are inserted into the lumen 24 of the tubular member 12, and the shaft 14 is advanced distally relative to the introducer until the balloon 16 is deployed out of the lumen 24 of the tubular member 12.

In other embodiments, the system 10 does not include the tubular member 12. In such cases, an introducer (not shown) with a sharp tip can be used. The introducer is inserted through the opening 700 and is used to puncture the liver 704. The introducer is then advanced until its distal tip punctures the target vessel 706, as similarly discussed. The introducer may have a rigid construction, which prevents bending of the introducer as it is inserted into the liver 704, and allows the introducer to be accurately positioned within the liver 704. In some embodiments, a wall of the introducer may include a plurality of fluid pockets, which allows the introducer to be imaged by ultrasound. In other embodiments, the introducer may include a radio-opaque marker secured to its distal end, which allows the introducer to be imaged by a fluoroscope or a x-ray device. Next, the balloon 16 and the shaft 14 are inserted into the lumen of the introducer, and the shaft 14 is advanced distally relative to the introducer until the balloon 16 is deployed out of the lumen of the introducer.

Figure 7C:
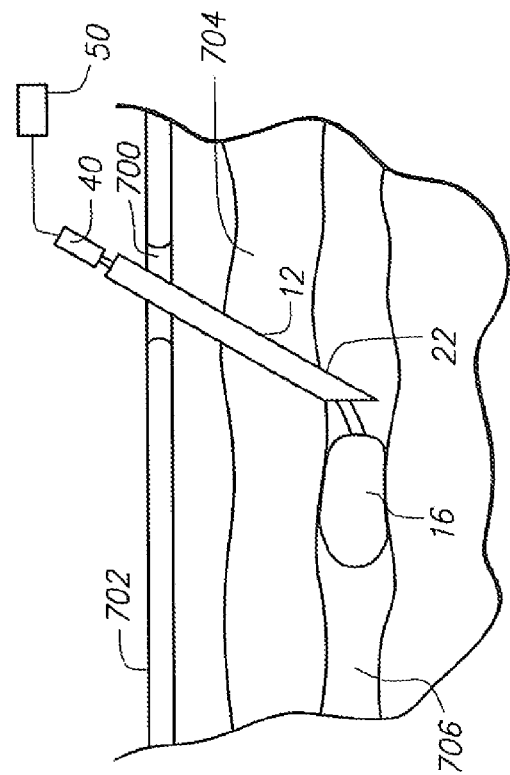

Next, inflation fluid, which can be gas or liquid, is delivered to the balloon 16 to inflate the balloon 16 (FIG. 7C). The balloon 16 is expanded until it substantially occludes the vessel 706, thereby preventing, or substantially reducing, flow of blood downstream. In the illustrated embodiments, before the balloon 16 is expanded, it is positioned away from the punctured opening 710 at the vessel 706. Such technique reduces the risk of rupturing the vessel 706 through the punctured opening 710 by the balloon 16 as it is inflated, which could occur if the balloon 16 is placed closely next to the punctured opening 710 at the vessel 706. In some embodiments, the balloon 16 includes the fluid pockets 102. The fluid pockets 102 may include gas, which allows the balloon 16 to be imaged by ultrasound, so that a physician can visualize the position of the balloon 16 as the balloon 16 is being positioned through the tubular member 12 and within the vessel 706. Alternatively, the fluid pockets 102 may include a radio-opaque liquid, which allows the balloon 16 to be imaged by other imaging techniques.

Figure 7D:
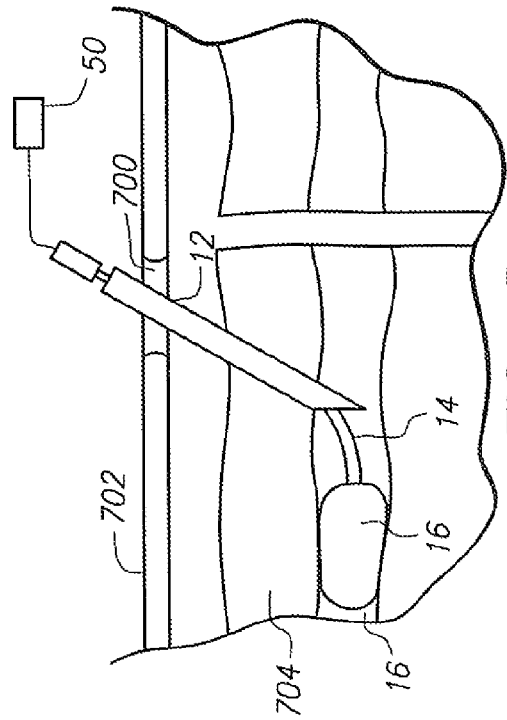

After the vessel 706 has been desirably occluded, the liver 704 is then resected (FIG. 7D). Such can be accomplished by using a surgical knife, an ablation device, or other cutting devices. As shown in the embodiments, because the vessel 706 is substantially occluded by the balloon 16, after the liver 704 has been resected, the amount of bleeding from the vessel 706 is prevented or substantially reduced. Although only one balloon 16 is used in the illustrated embodiments, in other embodiments, more than one balloons 16 can be used to occlude more than one vessel in the liver 704.

After bleeding has been prevented, the balloon 16 is then deflated and removed from the vessel 706.

In the above embodiments, the balloon 16 has been described as an occlusion device for occluding a vessel. In other embodiments, instead of a vessel, the balloon 16 can be sized to occlude other locations, such as an aneurysm, temporary vascular occlusion, within a patient's body. In further embodiments, instead of a liver, the balloon 16 can be used as an occlusion device in other parts of a patient's body, such as a heart, or a bronchi.

Also, in other embodiments, the balloon 16 can function as a dilator. For example, the balloon 16 can be delivered underneath a patient's skin, and is inflated to dilate a portion of the skin. In further embodiments, the balloon 16 can be used in a variety of medical procedures such as angioplasty where it is used to dilate a blood vessel.

In other embodiments, the balloon 16 functions as an anchor. For example, the balloon 16 can be delivered within a vessel, and is inflated to bear against a surface of the vessel to thereby secure itself against the vessel. In such cases, a medical device coupled to the balloon 16 is then anchored to the vessel.

In further embodiments, the balloon 16 functions as an ablation device. For example, the balloon 16 can be used in ablation procedures where they are used to deliver energy to tissue, such as heart tissue. In such case, the balloon 16 is typically carried at or adjacent a distal end of a catheter which, with the balloon 16 in a deflated configuration, is inserted into a patient's body, wherein the balloon 16 is inflated when it reaches a target site. Energy is then delivered to an electrode located in, or on the surface of, the balloon, which is transmitted to the target tissue. In some embodiments, the balloon 16 includes metallic dusts or metallic elements (e.g., made from foil) disposed on its surface, thereby forming one or more conductive regions on the balloon surface. Each conductive region functions as an electrode, and is secured to an electrode wire, which delivers electrical energy from a generator to the electrode.

In other embodiments, cold fluid can be delivered into the balloon 16, and the balloon 16 can then be used to remove energy from tissue to thereby injure the tissue.

Although the above embodiments of the system 10 have been described as having the balloon 16, in other embodiments, the system 10 may not include the balloon 16 and/or the shaft 14. For example, in further embodiments, the system 10 includes the tubular member 12, and not the balloon 16 and the shaft 14. In such cases, the tubular member 12 can be used to house or deliver other medical devices, such as an imaging device, an occlusive device, an anchoring device, a cutting device, an ablation device, or a biopsy device. At least a portion, e.g., the distal end 22, of the tubular member 12 includes the fluid pockets 202, which allows the portion to be imaged by ultrasound. The distal end 22 may have the sharp distal tip 23, or alternatively, a blunt tip. In some embodiments, the tubular member 12 has a rigid construction, which prevents the tubular member 12 from being bent during use. In other embodiments, the tubular member 12 is flexible. For example, the tubular member 12 can be a catheter, a microcatheter, or a sheath.

Thus, although several embodiments have been shown and described, it would be apparent to those skilled in the art that many changes and modifications may be made thereunto without the departing from the scope of the invention, which is defined by the following claims and their equivalents.

What is claimed:

1. A vessel occlusion apparatus, comprising:
an elongate shaft having a fluid delivery lumen; and
an expandable member carried on a distal end portion of the shaft, the expandable member comprising a body defining an interior region, the interior region in communication with the fluid delivery lumen, the body formed of a first sheet of material secured to a second sheet of material using an adhesive at selected locations, thereby creating a plurality of fluid pockets between the first sheet and the second sheet,
wherein the fluid pockets are fluidically isolated from any fluid lumens.

2. The apparatus of claim 1, wherein the fluid pockets have an elongated shape and contain a fluid that can be imaged using an imaging device, and wherein the elongated shape is configured for allowing a continuous portion of the expandable member body to be imaged using the imaging device.

3. The apparatus of claim 1, wherein the expandable member comprises an inflatable balloon.

4. The apparatus of claim 2, the fluid comprising a gas.

5. The apparatus of claim 2, the fluid comprising a liquid.

6. The apparatus of claim 2, the imaging device comprising a fluoroscopic imager.

7. The apparatus of claim 2, the imaging device comprising an ultrasound imager.

8. The apparatus of claim 1, wherein the expandable member is sized to occlude a blood vessel.

9. The apparatus of claim 1, wherein at least a portion of the expandable member body is electrically conductive.

10. The apparatus of claim 1, wherein the fluid pockets are rectangular.

11. The apparatus of claim 1, further comprising an elongate tubular delivery member having a lumen sized to accommodate insertion of the elongate shaft and expandable member there through.

12. An apparatus for use in a medical procedure, comprising:

an elongate tubular delivery member having a proximal portion, a distal portion, and a lumen extending between the proximal and distal portions, wherein the distal portion of the tubular member is formed of a first sheet of material secured to a second sheet of material using an adhesive at selected locations, thereby creating a plurality of fluid pockets between the first sheet and the second sheet, wherein the fluid pockets are fluidically isolated from any fluid lumens.

13. The apparatus of claim 12, wherein the distal portion of the tubular member comprises a tissue-piercing distal tip.

14. The apparatus of claim 12, wherein the fluid pockets have an elongated shape and contain a fluid that can be imaged using an imaging device, and wherein the elongated shape is configured for allowing a continuous portion of the distal portion of the tubular member to be imaged using the imaging device.

15. The apparatus of claim 14, the fluid comprising a gas.

16. The apparatus of claim 14, the fluid comprising a liquid.

17. The apparatus of claim 14, the imaging device comprising a fluoroscopic imager.

18. The apparatus of claim 14, the imaging device comprising an ultrasound imager.

19. The apparatus of claim 12, wherein the fluid pockets are rectangular.

20. The apparatus of claim 12, further comprising a balloon apparatus sized for insertion through the lumen of the tubular delivery member.

21. The apparatus of claim 20, wherein the balloon apparatus comprises an elongate shaft and an expandable member carried on a distal end portion of the elongate shaft.

22. The apparatus of claim 21, wherein the expandable member is sized to occlude a blood vessel.

* * * * *